United States Patent [19]

Blake et al.

[11] 4,069,170

[45] Jan. 17, 1978

[54] FLUIDIZED DEOXYCHLORINATION CATALYST COMPOSITION

[75] Inventors: Robert J. Blake, Oakland; Guy W. Roy, Richmond, both of Calif.

[73] Assignee: Stauffer Chemical Company, Westport, Conn.

[21] Appl. No.: 750,027

[22] Filed: Dec. 13, 1976

Related U.S. Application Data

[60] Continuation of Ser. No. 601,744, Aug. 4, 1975, abandoned, which is a continuation of Ser. No. 418,494, Nov. 23, 1973, abandoned, which is a continuation of Ser. No. 212,793, Dec. 27, 1971, abandoned, which is a division of Ser. No. 772,395, Oct. 31, 1968, Pat. No. 3,657,367.

[51] Int. Cl.$^2$ .............................................. B01J 27/06
[52] U.S. Cl. ................................. 252/441; 260/659 A
[58] Field of Search ......................................... 252/441

[56] References Cited

U.S. PATENT DOCUMENTS

| 2,636,864 | 4/1953 | Pye et al. ......................... 260/659 A |
| 3,427,359 | 2/1969 | Rectenwald et al. ........... 260/659 A |

FOREIGN PATENT DOCUMENTS 971,996   10/1964   United Kingdom.

*Primary Examiner*—Patrick P. Garvin
*Assistant Examiner*—William G. Wright
*Attorney, Agent, or Firm*—Michael J. Bradley

[57] ABSTRACT

Catalyst compositions comprising mixtures of salts of copper, potassium, didymium, lanthanum and magnesium are useful in the fluidized bed oxychlorination of aliphatic hydrocarbons. The catalyst composition loading is disposed on a suitable support media, preferably an alumina and does not cake or cause defluidization of the bed under start-up, operating, or shut-down conditions.

4 Claims, No Drawings

FLUIDIZED DEOXYCHLORINATION CATALYST COMPOSITION

This is a continuation of application Ser. No. 601,744 now abandoned, filed Aug. 4, 1975, which is a continuation of application Ser. No. 418,494 now abandoned, filed Nov. 23, 1973, which is a continuation of application Ser. No. 212,793 now abandoned, filed Dec. 27, 1971, which is a divisional of prior application Ser. No. 772,395, filed Oct. 31, 1968, now U.S. Pat. No. 3,657,367.

This invention relates to the oxychlorination of hydrocarbons. More particularly, the invention pertains to improved catalyst compositions and the utilization of said catalysts in aliphatic hydrocarbon oxychlorination processes.

The oxychlorination of hydrocarbon gases with a chlorinating agent and an oxygen containing gas is a well-known process in the prior art. It is customary to employ suitable catalysts which will accelerate the oxychlorination reaction. The catalysts usually employed comprise the salts, particularly the halides of metals having variable valances. These salts have been used as such in combination with various promoting substances, and in combination with or disposed upon mineral substances such as asbestos, diatomaceous earth, pumice, clay, kieselguhr, alumina, silica gel and the like. A particularly effective catalyst comprises a copper halide disposed upon an alumina support. The oxchlorination process has been carried out by passing a mixture of hydrogen chloride, chlorine, or a mixture of hydrogen chloride and chlorine, an oxygen containing gas, and the hydrocarbon through a reaction zone containing a fixed bed of the catalyst. More recently, however, the catalyst has come to be employed in a finely divided state according to the so-called fluidized catalyst technique. One of the disadvantages of the copper halide catalysts is that they are volatile at the required reaction temperatures. Thus, the catalyst mass is unable to retain its activity over an extended period of time due to loss of the copper halide which must be continually replaced or recovered and returned to the reaction zone. The problem of catalyst losses is aggravated when the catalyst is employed in the fluidized state. As a result of having the catalyst in the form of particles, the loss of the copper halide is even more pronounced and catalyst life is even shorter. The use of an alkali metal chloride as catalyst stabilizer reducing mobility of the copper salt component is to be recognized as well as its use as an oxidation inhibitor advantageous in reducing the catalyst loss according to U.S. Pat. No. 3,267,161. In addition to volatilization of the catalyst salts, a main catalyst disadvantage in fluidized beds is the catalyst's tendency to cake during its active life.

The term "oxychlorination" utilized herein the specification refers to metal halide catalyzed processes in which gaseous hydrogen chloride, chlorine or a mixture of hydrogen chloride and chlorine is used as a chlorinating agent. These processes involve chlorination of hydrocarbons or chlorohydrocarbons with a chlorinating agent and an oxygen containing gas such as air or elemental oxygen. The process takes place most efficiently in the presence of a metal halide catalyst such as cupric chloride impregnated on a suitable carrier. It has been postulated that in these oxychlorination processes, the hydrogen chloride is oxidized to chlorine and water and the chlorine reacts with the organic material present in the feed gas to form chlorinated hydrocarbons.

The term "fluidized bed" as employed herein this specification refers to processes in which a gas is passed through a catalyst bed of solid particulate material wherein several different conditions may be established depending upon the gas velocity, size of the catalyst particles, reactor size, and other reaction zone parameters. The state of normal fluidization exists when the gas flow rate is increased beyond the flow at which the upward thrust of the gas balances the weight of the particles. At this gas flow rate the bed height expands and the particles are set in violent, chaotic motion.

A major problem in fluid bed operations of oxychlorination processes has been the caking tendency of the available catalysts. This caking or agglomeration of the catalyst results in defluidization of the bed, as well as extremely high localized temperatures in the catalyst bed which makes it difficult to control the reaction and the products formed. A fluidized bed catalyst which is non-caking under operating, start-up or shut down conditions is essential to an economically operative oxychlorination process.

The principal object of this invention is to provide a non-caking catalyst for use in a fluidized bed oxychlorination process.

Another object is to provide an effective catalyst composition and method for the oxychlorination of hydrocarbons and the chlorinated derivatives thereof.

Yet another object is to provide an effective catalyst composition and method for the oxychlorination of methane in a fluidized bed.

Still another object is to provide an effective catalyst composition which will not cake during its active life when used in a fluid bed operation for the oxychlorination of hydrocarbons and the chloro derivatives thereof.

Further objects of this invention will become obvious to one skilled in the art from the detailed description which is contained herein below.

The objects of the invention are general accomplished by providing a gaseous mixture comprising a hydrocarbon or partially chlorinated hydrocarbon, an oxygen containing gas, and a chlorinating agent selected from the group consisting of hydrogen chloride, chlorine and mixtures of hydrogen chloride and chlorine, as feed material to a suitable oxychlorination reaction zone. The hydrocarbons or partially chlorinated hydrocarbons are aliphatic, saturated or unsaturated, hydrocarbons containing from one to four carbon atoms and the chlorinated derivatives thereof such as methane, ethane, butane, ethylene, methyl chloride and ethylene dichloride. The reaction zone is maintained at a temperature sufficient to effect the oxychlorination of the hydrocarbon or chlorinated hydrocarbon to the desired chlorinated hydrocarbon products. The feed mixture is contacted with a fluidized bed of catalyst suitable to effect the desired reaction in the contact time provided. The catalyst comprises a mixture of a catalytically effective percentage of $CuCl_2$, an alkali metal chloride selected from the group consisting of KCl and NaCl present in an amount sufficient to prevent substantial oxidation, didymium chloride and lanthanum chloride. It has been discovered that such catalyst mixtures containing both didymium and lanthanum chlorides remain fluid and do not tend to cake during the active life of the catalyst. Didymium chloride ($DiCl_3$) is a commercial mixture of rare earth chlorides containing a substantial percentage of lanthanum in the mixture (refer to Table I).

Table I
RARE EARTH COMPOSITION OF DIDYMIUM CHLORIDE

| Rare Earth | Rare Earth Composition - Per Cent | |
|---|---|---|
| | 100% Oxide Basis | As-Is Basis |
| Lanthanum | | |
| as $La_2O_3$ | 45–46 | 20.7 |
| as $LaCl_3 \cdot 6H_2O$ | — | 45.2 |
| Cerium | | |
| as $CeO_2$ | 1–2 | 0.5 |
| as $CeCl_3 6H_2O$ | — | 1.0 |
| Praseodymium | | |
| as $Pr_6O_{11}$ | 9–10 | 4.4 |
| as $PrCl_3 \cdot 6H_2O$ | — | 9.4 |
| Neodymium | | |
| as $Nd_2O_3$ | 32–33 | 14.6 |
| as $NdCl_3 \cdot 6H_2O$ | — | 30.3 |
| Samarium | | |
| as $Sm_2O_3$ | 5–6 | 2.5 |
| as $SmCl_3 \cdot 6H_2O$ | — | 5.2 |
| Gadolinium (approx.) | | |
| as $Gd_2O_3$ | 3–4 | 1.5 |
| as $GdCl_3 \cdot 6H_2O$ | — | 3.1 |
| Yttrium (approx.) | | |
| as $Y_2O_3$ | 0.4 | 0.2 |
| as $YCl_3 \cdot 6H_2O$ | — | 0.5 |
| Other rare earths (approx.) | | |
| as $R_2O_3$ | 1–2 | 0.6 |
| as $RCl_3 \cdot 6H_2O$ | — | 1.2 |
| TOTALS as oxides | 100 | 45 |
| as $RCl_3 \cdot 6H_2O$ | — | 95.9 |
| as Metals | — | 37.9 |

*Analysis provided by American Potash & Chemical Corp.

A preferred catalyst composition consists of from about 0.5% to about 15% $CuCl_2$; from about 0.1% to about 10% of an alkali metal chloride selected from the group consisting of KCl and NaCl; from about 0.1% to about 12% didymium chloride ($DiCl_3$); and from about 0.2% to about 6% $LaCl_3$. These percents are based on the total weight of catalyst composition plus support media. For any one catalyst composition, the total weight percent of the support media should be in the range of from about 75% to about 95%. The maximum total catalyst loading is about 25 weight percent and the minimum total catalyst loading is about 5 weight percent. The catalyst loading which is employed in a given case depends upon factors which include, e.g., temperature and reactant composition. The most preferred catalyst composition consists of from about 0.8% to about 10% $CuCl_2$, from about 0.5% to about 5% KCl, from about 2% to about 9% $DiCl_3$, and from about 1% to about 3% $LaCl_3$.

This catalyst composition is generally disposed on any suitable porous support material although preferred supports are hereinafter described. It has been discovered in the practice of the present invention that catalysts containing mixtures of salts of Cu, K, didymium and lanthanum disposed upon alpha-alumina as well as silica-alumina supports remain fluid, i.e., do not cake or agglomerate, under conditions of methane oxychlorination which are more fully hereinafter described.

It has also been discovered that catalysts containing certain support media employed in conjunction with the novel catalyst salt mixtures of the present invention remain fluid during operating conditions and yet cake during shut down or subsequent start up. Such catalysts can, by the addition of magnesium chloride to the salt composition, be inhibited from caking. The caking of these fluid bed catalysts is inhibited by the addition of from about 0.1% to about 2% (weight) $MgCl_2$ and it is preferred to use about 0.2% to about 1.0% $MgCl_2$ on a silica-alumina support having a surface area of about 1.5 to about 4 $m^2/gm$.

The catalyst support media is of considerable importance in the oxychlorination reaction. The surface areas of the support media have a direct effect on the promotion of side reactions which result in the oxidation of the hydrocarbons and their chloro derivatives. It has been determined that an increase in the surface area of the support media over 90 $m^2/gm$ increases these side reactions. The preferred range of surface area for the support media is about 1 to about 30 $m^2/gm$.

Support media such as silica gel, pumice, fullers earth, alumina, silica-alumina and diatomaceous earth are to be preferred. The most preferred support is alpha-alumina and silica-alumina having a surface area of from about 1 to about 30 $m^2/gm$ and a porosity range of from about 0.2 to about 0.45 cc/gm.

The particle size of the alpha-alumina and silica-alumina is in the range of from about 20 to about 200 microns. The preferred particle size range is from about 40 to about 150 microns.

Tables II and III show the related properties of typical catalyst support media.

TABLE II
CATALYST SUPPORTS

| Surface Area ($m^2/gm$) | α-Alumina (2–4) | Silica-Alumina (1.5–4) | α-Alumina (10–20) |
|---|---|---|---|
| Apparent Bulk Density (g/cc) | 1.10 | 0.97 | 1.1 |
| Tyler Mesh Sieve Analysis (Wt. % retained in designated range) | | | |
| + 80 Mesh | 0.5 | 13.8 | 0.9 |
| − 80 + 100 Mesh | 8.5 | 38.7 | 3.8 |
| −φ + 115 Mesh | 14.5 | 11.9 | 7.1 |
| −115 + 150 Mesh | 20.0 | 17.6 | 27.2 |
| − + 170 Mesh | 13.9 | 7.0 | 26.1 |
| −170 + 200 Mesh | 11.1 | 4.1 | 16.0 |
| −200 + 250 Mesh | 5.6 | 1.4 | 9.0 |
| −250 + 325 Mesh | 16.4 | 3.9 | 8.3 |
| −325 Mesh | 9.4 | 1.7 | 1.6 |
| Surface Area ($m^2/gm$) (measured) | 3.4 | 1.8 | 11.7 |

Table III
Alumina Supports

| Alumina Type | Apparent Bulk Density (gm/cc) | Surface Area ($m^2/gm$) | Porosity (cc/gm) | Support Composition (Weight %) | | | |
|---|---|---|---|---|---|---|---|
| | | | | $Al_2O_3$ | $SiO_2$ | $Fe_2O_3$ | $Na_2O$ |
| α-Alumina (2–4 $m^2/gm$) | 1.10 | 3.9 | 0.44 | 99.4 | 0.02 | 0.04 | 0.5 |
| Silica Alumina (1.5–4 $m^2/gm$) | 0.94 | 2.4 | 0.34 | 95.4 | 3.3 | 0.02 | 0.77 |
| α-Alumina (10–20 $m^2/gm$) | 1.1 | 16.8 | 0.30 | 99.0 | 0.02 | 0.03 | 0.45 |

In accordance with a preferred embodiment of the method of the present invention, gaseous methane is reacted with gaseous hydrogen chloride, chlorine or hydrogen chloride and chlorine and an oxygen containing gas in a reaction zone which is maintained at a temperature of between about 300° and about 600° C.; a preferred temperature range is between about 350° and about 450° C.

The uniformity of reaction temperature through the reaction zone is promoted by operating the catalyst in a fluid bed. This type of operation avoids the existence of hot spots in the catalyst bed which would increase the oxidation of hydrocarbon side reactions.

The contact time of the reactants in the reaction zone is an important parameter. The preferred residence time for the oxychlorination of methane is about 1 to about 20 seconds with the most preferred retention time being between about 2 and about 10 seconds.

Having thus described the invention in general terms, reference is now had to specific examples which have been carried out in accordance with the techniques of the present invention.

EXAMPLE 1

The catalytic system is prepared by mixing 125.1 gms $CuCl_2.2H_2O$, 54.7 gms KCl, 62.3 gms $LaCl_3.6H_2O$, and 232.3 gms $DiCl_3.6H_2O$ plus 476 gms water, thereby effecting a 40 weight percent solution of salts. The mixing was done at ambient conditions in a vessel of a size sufficient to contain the components therein.

The $DiCl_3.6H_2O$ analysis is shown in Table I.

The solution is then slowly poured onto 1504 gms of silica-alumina, having a surface area of 1.5-4 $m^2/gm$ and, a porosity of from about 0.2 to about 0.45 cc/gm and a particle size of from about 40 to about 150 microns, with mechanical mixing. The moist catalyst is then dried for 20 hours at 140° C.

The dried catalyst is then placed in a Pyrex reactor which consists of a vertical 20 inch Pyrex tubular lower portion with an internal diameter of 47 millimeters. The catalyst is supported in the tube by an extra coarse sintered disc which is placed within the tube at the lower end thereof and contained therein. The bottom of the tube is sealed except for an opening to allow the reaction gases to enter the tube below the sintered disc. The height of the static bed of the catalyst in the tubular section is 10 inches. Attached to the upper end of the tubular portion of the reactor is a tapered section, having its broader portion at the upper part thereof, to affect the separation of catalyst fines from the reaction gases. The top portion of the tapered section is affixed with an opening to allow the gaseous effluent to leave the reactor and to allow the insertion of a 10 millimeter outside diameter tube into the catalyst bed extending towards the bottom thereof. The tube has attached thereto, at the lower end thereof, a four-arm spider. The tube and four-arm spider are rotably mounted. The reactor is electrically heated and it is controlled automatically by means of a thermocouple and a temperature controller.

The catalyst bed is fluidized by 2.81 gram moles per hour of HCl, 2.81 gram moles per hour of $CH_4$ and 9.95 gram moles per hour of air. The combined flows result in a superficial velocity of 0.5 feet per second at an operating temperature of 440° C and a pressure of 1 atmosphere.

The gaseous effluent exiting from the top of the reactor is analysed by gas chromatograph and wet chemical methods. These analyses show that the results of the oxychloridation reaction is an 86% conversion of HCl, a 39% conversion of $CH_4$ to chlorinated methanes and a 2.6% oxidization of $CH_4$.

EXAMPLE II

In a reactor similar to that of Example I, the catalyst bed is fluidized by the additional flow of $CH_3Cl$ to produce chlorinated methanes.

EXAMPLE III

Using a reactor system similar to that of Example I, the bed is fluidized by a flow of gaseous ethylene dichloride, HCl and oxygen to produce perchloroethylene, trichloro ethylene and saturated chlorination products of a higher molecular weight than trichloroethylene.

EXAMPLE IV

The catalyst bed in a reactor system similar to that of Example I is fluidized by a flow of gaseous ethane, HCl and oxygen to produce chlorinated ethanes.

EXAMPLE V

The non-caking effect gained by addition of $LaCl_3$ to the catalyst salt loading containing $CuCl_2$, KCl, $DiCl_3$ is shown in the following Table IV. The catalysts are prepared in accordance to the method of Example I. The catalysts are tested for periods ranging up to 1780 hours in the reactor system set forth in Example I.

Table IV

| Support | Weight % of Metal Present (Based on salt composition plus support) | | | | Non-caking at 440° C | Caked at 440° C |
|---|---|---|---|---|---|---|
| | Cu | K | Di | La | | |
| α-alumina (2–4 $m^2/gm$) | 2.5 | 1.54 | 5.0 | 1.3 | X | |
| " | 2.5 | 0.77 | 5.0 | 1.3 | X | |
| " | 2.5 | 0 | 5.0 | 1.3 | X | |
| " | 1.25 | 0.77 | 2.5 | 0.66 | X | |
| " | 2.0 | 1.0 | 5.0 | — | | X |
| " | 1.8 | 0.9 | 2.5 | — | | X |

EXAMPLE VI

Comparisons of catalyst supports and catalyst salt loading compositions are made to evaluate the activity and fluidizing characteristics that would result. The experimental data is compiled in Tables V, VI and VII. The tables show that salt loading on a particular support with the percent HCl conversion to chlorinated methanes, the percent methane loss through oxidation and the tendency of the catalyst to cake under operating or shut down conditions. The effect of $LaCl_3$ and $MgCl_2$ addition can be clearly seen. The catalysts are prepared in accordance with the method of Example I and the bed heights were measured under static conditions.

Table V
LaCl₃ Addition Effect

| Support (Surface Area) | Salt Composition (Weight %) | | | | | Activity at 440° C 10 in. catalyst bed | | Fluid Bed Catalyst Characteristics (Reaction 440° C) |
|---|---|---|---|---|---|---|---|---|
| | CuCl₂ | KCl | DiCl₃ | LaCl₃ | MgCl₂ | % HCl Conversion | % CH₄ Oxidized | |
| α-Alumina (2–4 m²/gm) | 5.3 | 2.94 | 8.73 | 2.3 | — | 89 | 3.2 | Non-caking at operating conditions |
| " | 5.3 | 1.47 | 8.73 | 2.3 | — | 86 | 3.9 | " |
| " | 2.65 | 1.47 | 4.36 | 1.25 | — | 87 | 3.3 | " |
| " | 4.24 | 1.91 | 8.73 | — | — | — | — | Caked at operating conditions |
| " | 3.82 | 1.72 | 4.36 | — | — | — | — | " |

Table VI
MgCl₂ Addition Effect

| Support (Surface Area) | Salt Composition (Weight %) | | | | | Activity at 440° C 10 in. catalyst bed | | Fluid Bed Catalyst Characteristics (Reaction Temperature 440° C) |
|---|---|---|---|---|---|---|---|---|
| | CuCl₂ | KCl | DiCl₃ | LaCl₃ | MgCl₂ | % HCl Conversion | % CH₄ Oxidized | |
| α-Alumina (2–4 m²/gm) | 5.3 | 2.94 | 8.73 | 2.3 | — | 89 | 3.2 | Cakes on N₂ shut-down |
| " | 5.3 | 2.94 | 8.73 | 2.3 | 1.96 | 89 | 4.0 | No caking on N₂ shut-down |
| Silica-Alumina (1.5–4 m²/gm) | 5.3 | 2.94 | 8.73 | 2.3 | — | 87 | 2.6 | Cakes on N₂ shut-down |
| " | 2.65 | 1.45 | 4.37 | 1.16 | 0.39 | 90 | 2.4 | No caking on N₂ shut-down |

Table VII
High versus low surface area support media

| Support (Surface Area) | Salt Composition (Weight %) | | | | | Activity at 440° C 10 in. catalyst bed | | Fluid Bed Catalyst Characteristics (Reaction Temperature 440° C) |
|---|---|---|---|---|---|---|---|---|
| | CuCl₂ | KCl | DiCl₃ | LaCl₃ | MgCl₂ | % HCl Conversion | % CH₄ Oxidized | |
| α-Alumina (2–4 m²/gm) | 5.3 | 2.94 | 8.73 | 2.3 | — | 89 | 3.2 | No caking at operating conditions |
| " | 5.3 | 2.94 | 8.73 | 2.3 | — | 89 | 3.2 | Cakes on N₂ shut-down |
| α-Alumina (10–20 m²/gm) | 5.3 | 2.94 | 8.73 | 2.3 | — | 87 | 3.5 | No caking at operating conditions |
| " | 5.3 | 2.94 | 8.73 | 2.3 | — | 87 | 3.5 | No caking on N₂ shut-down |

EXAMPLE VII

Using a reactor similar to that of Example I, wherein the tubular lower portion is 32 inches in length with a catalyst bed height of 18 inches measured under static conditions, the following catalysts are tested. A CuCl₂, KCl, DiCl₃ and LaCl₃ salt composition is prepared as described in Example I and is absorbed on an alpha-alumina support. A salt composition of CuCl₂, KCl, DiCl₃, LaCl₃ and MgCl₂ is prepared by a method similar to that described in Example I and is absorbed on a silica-alumina support. A third catalyst is prepared by physically mixing equal parts of the first two catalysts prepared. The results of the tests are shown in Table VIII.

Table VIII

| Support (Surface Area) | Salt Composition (Weight %) | | | | | Activity at 440° C 18 in. catalyst bed | | Fluid Bed Catalyst Characteristics (Reaction Temperature 440° C) |
|---|---|---|---|---|---|---|---|---|
| | CuCl₂ | KCl | DiCl₃ | LaCl₃ | MgCl₂ | % HCl Conversion | % CH₄ Oxidized | |
| α-Alumina | 5.3 | 2.94 | 8.73 | 2.3 | — | 95.0 | 6.6 | Good fluidization at |

Table VIII-continued

| Support (Surface Area) | Salt Composition (Weight %) | | | | | Activity at 440° C 18 in. catalyst bed | | Fluid Bed Catalyst Characteristics (Reaction Temperature 440° C) |
|---|---|---|---|---|---|---|---|---|
| | CuCl$_2$ | KCl | DiCl$_3$ | LaCl$_3$ | MgCl$_2$ | % HCl Conversion | % CH$_4$ Oxidized | |
| (10-20 m$^2$/gm) Silica-Alumina | 2.65 | 1.47 | 4.37 | 1.16 | 0.39 | 96.0 | 3.6 | all temperatures Slugging on cool-down |
| (1.5-4 m$^2$/gm) 50/50 Mixture of above two | 3.98 | 2.2 | 6.55 | 1.73 | 0.2 | 96.0 | 5.1 | Good fluidization at all temperatures; Minimal slugging on cool-down |

The catalyst which is a combination of the CuCl$_2$, KCl, DiCl$_3$, LaCl$_3$ on an alpha-alumina support and the CuCl$_2$, KCl, DiCl$_3$, LaCl$_3$, MgCl$_2$ on a silica-alumina support does not separate into a zone of the alpha-alumina supported catalyst and a zone of the lighter silica alumina supported catalyst when it is fluidized. This combined catalyst has the advantage of high HCl to RCl conversion, R being a hydrocarbon of one to four carbon atoms; good fluidization over a temperature range of 30° C to 450° C and relatively low oxidation.

Having thus described the invention with reference to specific examples thereof, it is to be understood that other modifications, alterations and applications will become apparent to those skilled in the art without departing from the scope of the present invention and that the present invention is limited only as defined in the claims appended hereto.

We claim:

1. In a fluidized bed oxychlorination catalyst composition disposed upon an alpha-alumina support therefore which comprises a catalytically effective percentage of copper chloride, an oxidation inhibitor selected from the group consisting of sodium chloride and potassium chloride and between about 0.1 and about 12 percent by weight didymium chloride based upon the total weight of catalyst composition and support, the improvement comprising adding to the catalyst composition between about 0.2 to about 6 percent by weight additional lanthanum chloride above and beyond that lanthanum chloride contained in the didymium chloride.

2. The improved catalyst composition of claim 1 with a further improvement of adding between about 0.1 and about 2 weight percent MgCl$_2$.

3. In a fluidized bed oxychlorination catalyst composition disposed upon a support therefore selected from the group consisting of alpha-alumina, silica alumina and mixtures thereof comprises from about 0.8 to about 10 weight percent CuCl$_2$, from about 0.5 to about 6 weight percent KCl and from about 2 to about 9 weight percent DiCl$_3$, the improvement comprising adding from about 1 to about 3 weight percent lanthanum chloride based on the total weight of the catalyst composition and support above and beyond the lanthanum chloride contained in the didymium chloride of the catalyst composition.

4. The improved catalyst composition of claim 3 with a further improvement of adding from about 0.2 to about 1.0 weight percent magnesium chloride.

* * * * *

UNITED STATES PATENT AND TRADEMARK OFFICE
CERTIFICATE OF CORRECTION

PATENT NO. : 4,069,170
DATED : January 17, 1978
INVENTOR(S) : Robert J. Blake et al.

It is certified that error appears in the above-identified patent and that said Letters Patent are hereby corrected as shown below:

In Column 4, Table II, under Sieve Analysis:

"-0+ 115 mesh" should read "-100 + 115 mesh"

"-+170 mesh" should read "-150 + 170 mesh".

Signed and Sealed this

Twenty-seventh Day of June 1978

[SEAL]

Attest:

RUTH C. MASON
Attesting Officer

DONALD W. BANNER
Commissioner of Patents and Trademarks